(12) United States Patent
Schieber et al.

(10) Patent No.: US 9,610,196 B2
(45) Date of Patent: *Apr. 4, 2017

(54) OCULAR IMPLANTS WITH ASYMMETRIC FLEXIBILITY

(71) Applicant: IVANTIS, INC., Irvine, CA (US)

(72) Inventors: Andrew T. Schieber, Irvine, CA (US); Charles L. Euteneuer, St. Michael, MN (US)

(73) Assignee: IVANTIS, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/691,267

(22) Filed: Apr. 20, 2015

(65) Prior Publication Data

US 2015/0223983 A1    Aug. 13, 2015

Related U.S. Application Data

(63) Continuation of application No. 14/246,363, filed on Apr. 7, 2014, now Pat. No. 9,039,650, which is a continuation of application No. 12/236,225, filed on Sep. 23, 2008, now Pat. No. 8,734,377, which is a continuation-in-part of application No. 11/860,318, filed on Sep. 24, 2007, now Pat. No. 7,740,604.

(51) Int. Cl.
*A61F 9/007* (2006.01)
*A61F 2/14* (2006.01)
*A61F 2/16* (2006.01)

(52) U.S. Cl.
CPC ............ *A61F 9/00781* (2013.01); *A61F 2/14* (2013.01); *A61F 2/15* (2015.04)

(58) Field of Classification Search
CPC . A61F 9/00781; A61M 27/00; A61M 27/002; A61M 27/006; A61M 27/008
See application file for complete search history.

(56) References Cited

U.S. PATENT DOCUMENTS

| | | |
|---|---|---|
| 703,296 A | 6/1902 | Arnold |
| 1,601,709 A | 10/1926 | Windom |
| 2,716,983 A | 9/1955 | George et al. |
| 3,071,135 A | 1/1963 | Baldwin et al. |

(Continued)

FOREIGN PATENT DOCUMENTS

| | | |
|---|---|---|
| AU | 1998/76197 B2 | 2/1999 |
| CN | 1950091 A | 4/2007 |

(Continued)

OTHER PUBLICATIONS

Wardle et al.; U.S. Appl. No. 14/363,409 entitled "Delivering ocular implants into the eye," filed Jun. 6, 2014.

(Continued)

*Primary Examiner* — Andrew Iwamaye
*Assistant Examiner* — Leslie Lopez
(74) *Attorney, Agent, or Firm* — Shay Glenn LLP

(57) ABSTRACT

An ocular implant having an inlet portion and a Schlemm's canal portion distal to the inlet portion, the inlet portion being disposed at a proximal end of the implant and sized and configured to be placed within an anterior chamber of a human eye, the Schlemm's canal portion being arranged and configured to be disposed within Schlemm's canal of the eye when the inlet portion is disposed in the anterior chamber.

10 Claims, 11 Drawing Sheets

(56) References Cited

U.S. PATENT DOCUMENTS

| | | |
|---|---|---|
| 3,788,327 A | 1/1974 | Donowitz et al. |
| 3,811,442 A | 5/1974 | Maroth |
| 3,948,271 A | 4/1976 | Akiyama |
| 4,037,604 A | 7/1977 | Newkirk |
| 4,428,746 A | 1/1984 | Mendez |
| 4,457,757 A | 7/1984 | Molteno |
| 4,601,713 A | 7/1986 | Fuqua |
| 4,689,040 A | 8/1987 | Thompson |
| 4,699,140 A | 10/1987 | Holmes et al. |
| 4,706,669 A | 11/1987 | Schlegel |
| 4,722,724 A | 2/1988 | Schocket |
| 4,733,665 A | 3/1988 | Palmaz |
| 4,750,901 A | 6/1988 | Molteno |
| 4,826,478 A | 5/1989 | Schocket |
| 4,861,341 A | 8/1989 | Woodburn |
| 4,880,000 A | 11/1989 | Holmes et al. |
| 4,886,488 A | 12/1989 | White |
| 4,919,130 A | 4/1990 | Stoy et al. |
| 4,934,363 A | 6/1990 | Smith et al. |
| 4,934,809 A | 6/1990 | Volk |
| 4,936,825 A | 6/1990 | Ungerleider |
| 4,946,436 A | 8/1990 | Smith |
| 4,968,296 A | 11/1990 | Ritch et al. |
| 5,092,837 A | 3/1992 | Ritch et al. |
| 5,127,901 A | 7/1992 | Odrich |
| 5,178,604 A | 1/1993 | Baerveldt et al. |
| 5,180,362 A | 1/1993 | Worst |
| 5,190,552 A | 3/1993 | Kelman |
| 5,213,569 A | 5/1993 | Davis |
| 5,246,452 A | 9/1993 | Sinnott |
| 5,290,267 A | 3/1994 | Zimmermann |
| 5,360,399 A | 11/1994 | Stegmann |
| 5,372,577 A | 12/1994 | Ungerleider |
| 5,445,637 A | 8/1995 | Bretton |
| 5,454,796 A | 10/1995 | Krupin |
| 5,458,615 A | 10/1995 | Klemm et al. |
| 5,536,259 A | 7/1996 | Utterberg |
| 5,575,780 A | 11/1996 | Saito |
| 5,591,223 A | 1/1997 | Lock et al. |
| 5,613,972 A | 3/1997 | Lee et al. |
| 5,626,558 A | 5/1997 | Suson |
| 5,653,753 A | 8/1997 | Brady et al. |
| 5,676,669 A | 10/1997 | Colvard |
| 5,792,099 A | 8/1998 | DeCamp et al. |
| 5,807,302 A | 9/1998 | Wandel |
| 5,865,831 A | 2/1999 | Cozean et al. |
| 5,868,697 A | 2/1999 | Richter et al. |
| 5,879,319 A | 3/1999 | Pynson et al. |
| 5,893,837 A | 4/1999 | Eagles et al. |
| 5,919,171 A | 7/1999 | Kira et al. |
| 5,948,427 A | 9/1999 | Yamamoto et al. |
| 5,968,058 A | 10/1999 | Richter et al. |
| 6,007,511 A | 12/1999 | Prywes |
| 6,050,970 A | 4/2000 | Baerveldt |
| 6,102,045 A | 8/2000 | Nordquist et al. |
| 6,186,974 B1 | 2/2001 | Allan et al. |
| 6,217,584 B1 | 4/2001 | Nun |
| 6,221,078 B1 | 4/2001 | Bylsma |
| 6,238,409 B1 | 5/2001 | Hojeibane |
| 6,241,721 B1 | 6/2001 | Cozean et al. |
| D444,874 S | 7/2001 | Haffner et al. |
| 6,328,747 B1 | 12/2001 | Nun |
| 6,375,642 B1 | 4/2002 | Grieshaber et al. |
| 6,409,752 B1 | 6/2002 | Boatman et al. |
| 6,450,984 B1 | 9/2002 | Lynch et al. |
| 6,464,724 B1 | 10/2002 | Lynch et al. |
| 6,471,666 B1 | 10/2002 | Odrich |
| 6,494,857 B1 | 12/2002 | Neuhann |
| 6,508,779 B1 | 1/2003 | Suson |
| 6,517,523 B1 | 2/2003 | Kaneko et al. |
| 6,524,275 B1 | 2/2003 | Lynch et al. |
| 6,533,764 B1 | 3/2003 | Haffner et al. |
| 6,533,768 B1 | 3/2003 | Hill |
| 6,544,208 B2 | 4/2003 | Ethier et al. |
| 6,544,249 B1 | 4/2003 | Yu et al. |
| 6,551,289 B1 | 4/2003 | Higuchi et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,699,211 B2 | 3/2004 | Savage |
| 6,702,790 B1 | 3/2004 | Ross |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,198 B2 | 4/2005 | Brown |
| 6,899,717 B2 | 5/2005 | Weber et al. |
| 6,939,298 B2 | 9/2005 | Brown et al. |
| 6,955,656 B2 | 10/2005 | Bergheim et al. |
| 6,962,573 B1 | 11/2005 | Wilcox |
| 6,981,958 B1 | 1/2006 | Gharib et al. |
| 6,989,007 B2 | 1/2006 | Shadduck |
| 7,094,225 B2 | 8/2006 | Tu et al. |
| 7,135,009 B2 | 11/2006 | Tu et al. |
| 7,147,650 B2 | 12/2006 | Lee |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,488,303 B1 | 2/2009 | Haffner et al. |
| 7,699,882 B2 | 4/2010 | Stamper et al. |
| 7,740,604 B2 | 6/2010 | Schieber et al. |
| 7,931,596 B2 | 4/2011 | Rachlin et al. |
| 7,967,772 B2 | 6/2011 | McKenzie et al. |
| 8,012,115 B2 | 9/2011 | Karageozian |
| 8,123,729 B2 | 2/2012 | Yamamoto et al. |
| 8,267,882 B2 | 9/2012 | Euteneuer et al. |
| 8,282,592 B2 | 10/2012 | Schieber et al. |
| 8,337,509 B2 | 12/2012 | Schieber et al. |
| 8,372,026 B2 | 2/2013 | Schieber et al. |
| 8,414,518 B2 | 4/2013 | Schieber et al. |
| 8,425,449 B2 | 4/2013 | Wardle et al. |
| 8,512,404 B2 | 8/2013 | Frion et al. |
| 8,529,494 B2 | 9/2013 | Euteneuer et al. |
| 8,551,166 B2 | 10/2013 | Schieber et al. |
| 8,657,776 B2 | 2/2014 | Wardle et al. |
| 8,663,150 B2 | 3/2014 | Wardle et al. |
| 8,734,377 B2 | 5/2014 | Schieber et al. |
| 8,808,222 B2 | 8/2014 | Schieber et al. |
| 8,945,038 B2 | 2/2015 | Yablonski |
| 8,961,447 B2 | 2/2015 | Schieber et al. |
| 9,039,650 B2 | 5/2015 | Schieber et al. |
| 9,050,169 B2 | 6/2015 | Schieber et al. |
| 9,066,750 B2 | 6/2015 | Wardle et al. |
| 9,066,783 B2 | 6/2015 | Euteneuer et al. |
| 2001/0002438 A1 | 5/2001 | Sepetka et al. |
| 2002/0003546 A1 | 1/2002 | Mochimaru et al. |
| 2002/0013546 A1 | 1/2002 | Grieshaber et al. |
| 2002/0013572 A1 | 1/2002 | Berlin |
| 2002/0052653 A1 | 5/2002 | Durgin |
| 2002/0072673 A1 | 6/2002 | Yamamoto et al. |
| 2002/0133168 A1 | 9/2002 | Smedley et al. |
| 2002/0143284 A1 | 10/2002 | Tu et al. |
| 2002/0165504 A1 | 11/2002 | Sharp et al. |
| 2002/0193805 A1 | 12/2002 | Ott et al. |
| 2003/0004457 A1 | 1/2003 | Andersson |
| 2003/0040754 A1* | 2/2003 | Mitchell ............... A61F 2/07 606/106 |
| 2003/0055372 A1 | 3/2003 | Lynch et al. |
| 2003/0060748 A1 | 3/2003 | Baikoff |
| 2003/0060752 A1 | 3/2003 | Bergheim et al. |
| 2003/0060784 A1 | 3/2003 | Hilgers et al. |
| 2003/0093084 A1 | 5/2003 | Nissan et al. |
| 2003/0097151 A1 | 5/2003 | Smedley et al. |

(56) References Cited

U.S. PATENT DOCUMENTS

| | | |
|---|---|---|
| 2003/0181848 A1 | 9/2003 | Bergheim et al. |
| 2003/0187384 A1 | 10/2003 | Bergheim et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0024453 A1 | 2/2004 | Castillejos |
| 2004/0030302 A1 | 2/2004 | Kamata et al. |
| 2004/0082939 A1 | 4/2004 | Berlin |
| 2004/0088048 A1 | 5/2004 | Richter et al. |
| 2004/0098124 A1 | 5/2004 | Freeman et al. |
| 2004/0102729 A1 | 5/2004 | Haffner et al. |
| 2004/0106975 A1 | 6/2004 | Solovay et al. |
| 2004/0111050 A1 | 6/2004 | Smedley et al. |
| 2004/0122380 A1 | 6/2004 | Utterberg |
| 2004/0127843 A1 | 7/2004 | Tu et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0199171 A1 | 10/2004 | Akahoshi |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225357 A1 | 11/2004 | Worst et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0041200 A1 | 2/2005 | Rich |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0125003 A1 | 6/2005 | Pinchuk et al. |
| 2005/0131514 A1 | 6/2005 | Hijlkema et al. |
| 2005/0149114 A1 | 7/2005 | Cartledge et al. |
| 2005/0154443 A1 | 7/2005 | Linder et al. |
| 2005/0165385 A1 | 7/2005 | Simon |
| 2005/0192527 A1 | 9/2005 | Gharib et al. |
| 2005/0197667 A1 | 9/2005 | Chan et al. |
| 2005/0203542 A1 | 9/2005 | Weber et al. |
| 2005/0209549 A1 | 9/2005 | Bergheim et al. |
| 2005/0209550 A1 | 9/2005 | Bergheim et al. |
| 2005/0244464 A1 | 11/2005 | Hughes |
| 2005/0250788 A1 | 11/2005 | Tu et al. |
| 2005/0260186 A1 | 11/2005 | Bookbinder et al. |
| 2005/0266047 A1 | 12/2005 | Tu et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0288619 A1 | 12/2005 | Gharib et al. |
| 2005/0288745 A1 | 12/2005 | Andersen et al. |
| 2006/0020247 A1 | 1/2006 | Kagan et al. |
| 2006/0032507 A1 | 2/2006 | Tu |
| 2006/0052879 A1 | 3/2006 | Kolb |
| 2006/0069340 A1 | 3/2006 | Simon |
| 2006/0074375 A1 | 4/2006 | Bergheim et al. |
| 2006/0079828 A1 | 4/2006 | Brown |
| 2006/0084907 A1 | 4/2006 | Bergheim et al. |
| 2006/0106370 A1 | 5/2006 | Baerveldt et al. |
| 2006/0116626 A1 | 6/2006 | Smedley et al. |
| 2006/0149194 A1 | 7/2006 | Conston et al. |
| 2006/0154981 A1 | 7/2006 | Klimko et al. |
| 2006/0155238 A1 | 7/2006 | Shields |
| 2006/0155300 A1 | 7/2006 | Stamper et al. |
| 2006/0167421 A1 | 7/2006 | Quinn |
| 2006/0167466 A1 | 7/2006 | Dusek |
| 2006/0173397 A1 | 8/2006 | Tu et al. |
| 2006/0178674 A1 | 8/2006 | McIntyre |
| 2006/0189915 A1 | 8/2006 | Camras et al. |
| 2006/0189916 A1 | 8/2006 | Bas |
| 2006/0189917 A1 | 8/2006 | Mayr et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0241749 A1 | 10/2006 | Tu et al. |
| 2006/0264971 A1 | 11/2006 | Akahoshi |
| 2006/0276759 A1 | 12/2006 | Kinast et al. |
| 2007/0010827 A1 | 1/2007 | Tu et al. |
| 2007/0027452 A1 | 2/2007 | Varner et al. |
| 2007/0073275 A1 | 3/2007 | Conston et al. |
| 2007/0088432 A1 | 4/2007 | Solovay et al. |
| 2007/0106200 A1 | 5/2007 | Levy |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0135681 A1 | 6/2007 | Chin et al. |
| 2007/0179520 A1 | 8/2007 | West |
| 2007/0191863 A1 | 8/2007 | De Juan, Jr. et al. |
| 2007/0202186 A1 | 8/2007 | Yamamoto et al. |
| 2007/0219509 A1 | 9/2007 | Tashiro et al. |
| 2007/0265582 A1 | 11/2007 | Kaplan et al. |
| 2007/0270945 A1 | 11/2007 | Kobayashi et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2007/0293872 A1 | 12/2007 | Peyman |
| 2007/0298068 A1 | 12/2007 | Badawi et al. |
| 2008/0015488 A1 | 1/2008 | Tu et al. |
| 2008/0045878 A1 | 2/2008 | Bergheim et al. |
| 2008/0058704 A1 | 3/2008 | Hee et al. |
| 2008/0228127 A1 | 9/2008 | Burns et al. |
| 2008/0288082 A1 | 11/2008 | Deal |
| 2008/0312661 A1 | 12/2008 | Downer et al. |
| 2009/0005852 A1 | 1/2009 | Gittings et al. |
| 2009/0028953 A1 | 1/2009 | Yamamoto et al. |
| 2009/0030363 A1 | 1/2009 | Gellman |
| 2009/0030381 A1 | 1/2009 | Lind et al. |
| 2009/0036843 A1 | 2/2009 | Erskine |
| 2009/0043321 A1 | 2/2009 | Conston et al. |
| 2009/0054723 A1 | 2/2009 | Khairkhahan et al. |
| 2009/0069786 A1 | 3/2009 | Vesely et al. |
| 2009/0082862 A1 | 3/2009 | Schieber et al. |
| 2009/0104248 A1 | 4/2009 | Rapacki et al. |
| 2009/0138081 A1 | 5/2009 | Bergheim et al. |
| 2009/0182421 A1 | 7/2009 | Silvestrini et al. |
| 2009/0198248 A1 | 8/2009 | Yeung et al. |
| 2009/0204053 A1 | 8/2009 | Nissan et al. |
| 2009/0247955 A1 | 10/2009 | Yamamoto et al. |
| 2009/0259126 A1 | 10/2009 | Saal et al. |
| 2009/0281520 A1 | 11/2009 | Highley et al. |
| 2010/0004580 A1 | 1/2010 | Lynch et al. |
| 2010/0057072 A1 | 3/2010 | Roman et al. |
| 2010/0114309 A1 | 5/2010 | de Juan et al. |
| 2010/0137981 A1 | 6/2010 | Silvestrini et al. |
| 2010/0173866 A1 | 7/2010 | Hee et al. |
| 2010/0234726 A1 | 9/2010 | Sirimanne et al. |
| 2010/0234790 A1 | 9/2010 | Tu et al. |
| 2011/0009874 A1 | 1/2011 | Wardle et al. |
| 2011/0098809 A1 | 4/2011 | Wardle et al. |
| 2011/0319806 A1 | 12/2011 | Wardle |
| 2012/0010702 A1 | 1/2012 | Stegmann et al. |
| 2013/0150959 A1 | 6/2013 | Schieber et al. |
| 2013/0182223 A1 | 7/2013 | Wardle et al. |
| 2013/0231603 A1 | 9/2013 | Wardle et al. |
| 2013/0281907 A1 | 10/2013 | Wardle et al. |
| 2014/0066821 A1 | 3/2014 | Friedland et al. |
| 2014/0114229 A1 | 4/2014 | Wardle et al. |
| 2014/0249463 A1 | 9/2014 | Wardle et al. |
| 2015/0119787 A1 | 4/2015 | Wardle et al. |

FOREIGN PATENT DOCUMENTS

| | | |
|---|---|---|
| DE | 4226476 C1 | 8/1993 |
| DE | 19840047 A1 | 3/2000 |
| EP | 1615604 B1 | 8/2009 |
| EP | 2193821 A1 | 6/2010 |

(56) References Cited

FOREIGN PATENT DOCUMENTS

| | | |
|---|---|---|
| EP | 1715827 B1 | 12/2010 |
| EP | 2380622 A1 | 10/2011 |
| EP | 2468327 A1 | 6/2012 |
| EP | 2471563 A1 | 7/2012 |
| EP | 1833440 B1 | 8/2012 |
| JP | H10-504978 A | 5/1998 |
| JP | 11123205 | 5/1999 |
| JP | 2002541976 | 12/2002 |
| JP | 2002541977 | 12/2002 |
| JP | 2002542872 | 12/2002 |
| JP | 2006517848 | 8/2006 |
| JP | 2006289075 A | 10/2006 |
| JP | 2010509003 | 3/2010 |
| JP | 2011502649 | 1/2011 |
| WO | WO 00/07525 A1 | 2/2000 |
| WO | WO 00/64389 A1 | 11/2000 |
| WO | WO 00/64393 A1 | 11/2000 |
| WO | WO 01/97727 A1 | 12/2001 |
| WO | WO 02/36052 A1 | 5/2002 |
| WO | WO 02/074052 A2 | 9/2002 |
| WO | WO 02/080811 A2 | 10/2002 |
| WO | WO 03/015659 A2 | 2/2003 |
| WO | WO 03/045290 A1 | 6/2003 |
| WO | WO 2004/054643 A1 | 7/2004 |
| WO | WO 2004/093761 A1 | 11/2004 |
| WO | WO 2005/105197 A2 | 11/2005 |
| WO | WO 2006/066103 A2 | 6/2006 |
| WO | WO 2007/035356 A2 | 3/2007 |
| WO | WO 2007/047744 A2 | 4/2007 |
| WO | WO 2007/087061 A2 | 8/2007 |
| WO | WO 2008/002377 A1 | 1/2008 |
| WO | WO 2008/005873 A2 | 1/2008 |
| WO | WO 2009/120960 A2 | 10/2009 |

OTHER PUBLICATIONS

Schieber et al.; U.S. Appl. No. 14/692,442 entitled "Methods and apparatus for delivering ocular implants into the eye," filed Apr. 21, 2015.
Schieber et al.; U.S. Appl. No. 14/693,582 entitled "Methods and apparatus for delivering ocular implants into the eye," filed Apr. 22, 2015.
Schiber et al.; U.S. Appl. No. 14/440,610 entitled "Apparatus for delivering ocular implants into an anterior chamber of the eye," filed May 5, 2015.
Euteneuer et al.; U.S. Appl. No. 14/717,744 entitled "Methods and apparatus for treating glaucoma," filed May 20, 2015.

Bahler, et al.; Trabecular bypass stents decrease intraocular pressure in cultured human anterior segments; Amer. Journal of Ophthalmology; vol. 138, No. 6; pp. 988-994.e2; Dec. 2004.
D'Ermo, et al.; Our results with the operation of ab externo trabeculotomy; Ophthalmologica; vol. 163; pp. 347-355; Feb. 1971.
Ellingsen et al.; Trabeculotomy and sinusotomy in enucleated human eyes; Investigative Ophthalmology; vol. 11; pp. 21-28; Jan. 1972.
Grant; Experimental aqueous perfusion in enucleated human eyes; Archives of Ophthalmology; vol. 69; pp. 783-801; Jun. 1963.
Johnstone et al.; "Microsurgery of Schlemm's Canal and the Human Aqueous Outflow System;" American Journal of Ophthalmology, vol. 76 (6): 906-917; Dec. 1973.
Lee et al.; Aqueous-venous shunt and intraocular pressure. Preliminary report of animal studies; Investigative Ophthalmology; vol. 5; No. 1; pp. 59-64; Feb. 1966.
Moses, Robert; The effect of intraocular pressure on resistance to outflow; Survey of Ophthalmology; vol. 22; No. 2; pp. 88-100; Sep.-Oct. 1977.
Mäepea et al.; The pressures in the episcleral veins, schlemm's canal and the trabecular meshwork in monkeys: effects of changes in intraocular pressure; Exp. Eye Res.; vol. 49; pp. 645-663; Oct. 1989.
Rosenquist et al.; Outflow resistance of enucleated human eyes at two different perfusion pressures and different extents of trabeculotomy; Current Eye Res.; vol. 8; No. 12; pp. 1233-1240; Dec. 1989.
Savage, James; Gonioscopy in the management of glaucoma; Am. Academy of Ophthalmology; Focal Points; vol. XXIV; No. 3; pp. 1-14; Mar. 2006.
Schultz, Jared; Canaloplasty procedure shows promise for open-angle glaucoma in European study; Ocular Surgery News; vol. 34; Mar. 1, 2007.
Smit et al.; Effects of viscoelastic injection into schlemm's canal in primate and human eyes; J. Am. Academy of Ophthalmology; vol. 109; No. 4; pp. 786-792; Apr. 2002.
Spiegel et al.; Schlemm's canal implant: a new method to lower intraocular pressure in patients with POAG?; Ophthalmic Surgery and Lasers; vol. 30; No. 6; pp. 492-494; Jun. 1999.
Schieber et al.; U.S. Appl. No. 14/843,563 entitled "Ocular implants for delivery into the eye," filed Sep. 2, 2015.
Lynch, Mary G.; Prov. U.S. Appl. No. 60/131,030 entitled "Devices and methods for treating glaucoma by enhancing aqueous outflow through schlemm's canal and anterior chamber angle ," filed Apr. 26, 1999.

\* cited by examiner

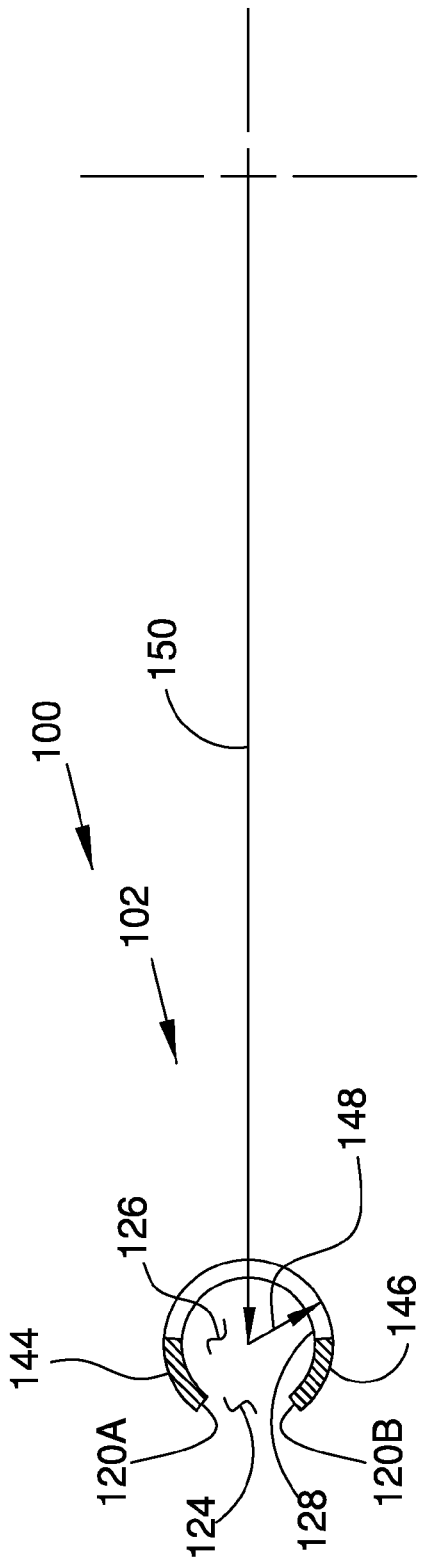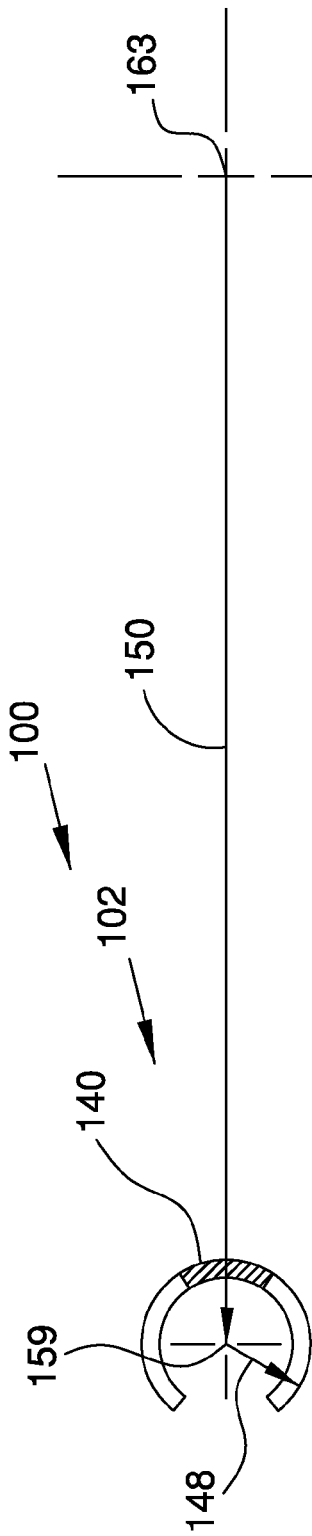

OCULAR IMPLANTS WITH ASYMMETRIC FLEXIBILITY

CROSS REFERENCE TO RELATED APPLICATIONS

This application is a continuation of U.S. application Ser. No. 14/246,363, filed Apr. 7, 2014, now U.S. Pat. No. 9,039,650; which is a continuation of U.S. application Ser. No. 12/236,225, filed Sep. 23, 2008, now U.S. Pat. No. 8,734,377, which is a continuation-in-part of U.S. application Ser. No. 11/860,318, filed Sep. 24, 2007, now U.S. Pat. No. 7,740,604, the disclosures of which are incorporated by reference as if fully set forth herein.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to devices that are implanted within the eye. More particularly, the present invention relates to devices that facilitate the transfer of fluid from within one area of the eye to another area of the eye.

BACKGROUND OF THE INVENTION

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modern tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid know as aqueous humor. Whenever a person views an object, he or she is viewing that object through both the vitreous humor and the aqueous humor.

Whenever a person views an object, he or she is also viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried along with the venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," Investigative Ophthalmology (February 1966)). Other early glaucoma treatment implants led from the anterior chamber to a sub-conjunctival bleb (e.g., U.S. Pat. No. 4,968,296 and U.S. Pat. No. 5,180,362). Still others were shunts leading from the anterior chamber to a point just inside Schlemm's canal (Spiegel et al., "Schlemm's canal implant: a new method to lower intraocular pressure in patients with POAG?" Ophthalmic Surgery and Lasers (June 1999); U.S. Pat. No. 6,450,984; U.S. Pat. No. 6,450,984). In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," Investigative Ophthalmology (February 1966)). Other early glaucoma treatment implants led from the anterior chamber to a sub-conjunctival bleb (e.g., U.S. Pat. No. 4,968,296 and U.S. Pat. No. 5,180,362). Still others were shunts leading from the anterior chamber to a point just inside Schlemm's canal (Spiegel et al., "Schlemm's canal implant: a new method to lower intraocular pressure in patients with POAG?" Ophthalmic Surgery and Lasers (June 1999); U.S. Pat. No. 6,450,984; U.S. Pat. No. 6,450,984).

SUMMARY OF THE INVENTION

While some prior glaucoma treatment implants did provide a flow path between the anterior chamber and Schlemm's canal, these prior devices failed to recognize (1) the importance of supporting a significant portion of Schlemm's canal in a patent state or (2) the harm to adjacent tissue caused by relatively high fluid flow rates at or around any portion of the device. The ocular implant devices and methods of this invention address one or both of these design criteria.

According to one aspect of the invention, the ocular implant may be inserted into Schlemm's canal of an eye to facilitate the flow of aqueous humor out of the anterior chamber of the eye by, e.g., supporting tissue in the trabecular meshwork and in Schlemm's canal. The flow facilitated by the presence of the ocular implant may include axial flow along Schlemm's canal, flow into Schlemm's canal from the anterior chamber of the eye, and flow leaving Schlemm's canal via the outlets that communicate with the canal.

After exiting Schlemm's canal via the outlets, aqueous humor enters the venous blood stream and is carried along with the venous blood leaving the eye. The pressure of the venous system tends to be around 5-10 mm Hg above atmospheric pressure. Accordingly, the venous system provides a pressure backstop which assures that the pressure in the anterior chamber of the eye remains above atmospheric pressure.

Some exemplary ocular implants according to this invention have a body with a plurality of open areas, strut areas and spine areas formed therein. The strut areas and spine areas act as reinforcing structures that hold the walls of Schlemm's canal in a patent state so that the walls of the canal provide a flow channel or fistula. Furthermore, the spine areas and the strut areas may be sized and shaped to reinforce Schlemm's canal while occupying a relatively small portion of the total lateral cross sectional area of Schlemm's canal. When this is the case, the ocular implant provides minimal obstruction to aqueous humor flowing along the length of Schlemm's canal. Reinforcing Schlemm's canal with minimal metal mass present in the canal may also encourage a safe healing response over time.

Some exemplary ocular implants according to this invention have a body defining openings that are sized and shaped to facilitate the lateral flow of aqueous humor across and/or through the body of the ocular implant. The lateral flow of aqueous humor may include the flow of aqueous humor through the trabecular mesh and into Schlemm's canal. The lateral flow of aqueous humor may also include the flow of aqueous humor through outlets that communicate with Schlemm's canal.

One aspect of the invention provides an ocular implant having a body extending along a generally curved longitudinal axis, the curved longitudinal axis defining a first plane, the body having a diameter of between 0.005 inches and 0.04 inches and being adapted to be disposed within a canal of Schlemm in a human subject's eye; wherein the body has a first flexibility when bent along the first plane and a second flexibility different from the first flexibility when bent along a second plane that intersects the first plane and is not coincident with the first plane, such as, e.g., a plane orthogonal to the first plane. In some embodiments, the body has a shape that is symmetric about the first plane.

The implant of the invention may have a variety of features. In some embodiments, the implant body has circumferential material coverage in cross-sections perpendicular to the longitudinal axis that is less than 360 degrees over an entire length of the body. The body may define an elongate slot that opens radially outward when the body is unrestrained.

In some embodiments, the body has a plurality of pairs of tissue supporting frames and a spine attached to each adjacent pair of tissue supporting frames. Each spine may have a shape that is symmetric about the first plane, and each tissue supporting frame may have a shape that is symmetric about the first plane. In some embodiments, the spines are longitudinally aligned with one another.

In some embodiments, each spine has a first minor side, a first major side, a second minor side, and a second major side; with each spine having a thickness extending between at least one point on each major side and at least one point on the second major side; each spine having a width extending between at least one point on each minor side and at least one point on the second minor side; and an aspect ratio of the width to the thickness being greater than about 2. In some embodiments, the first major side and the second major side are opposite one another. Also, the first major side may have a concave surface, and the second major side may have a convex surface. The concave surface and the convex surface may be concentric.

In some embodiments, each tissue supporting frame has at least a first strut and a second strut. Each strut may follow, e.g., a circumferentially undulating path while extending longitudinally between a first spine and a second spine.

In some embodiments, each strut has a first minor side, a first major side, a second minor side, and a second major side. In such embodiments, each strut has a thickness extending between at least one point on the first major side and at least one point on the second major side; a width extending between at least one point on the first minor side and at least one point on the second minor side; and an aspect ratio of the width to the thickness being greater than about 2. In some embodiments, the first major side and the second major side are opposite one another. Also, the first major side may have a concave surface, and the second major side may have a convex surface. The concave surface and the convex surface may be concentric.

In some embodiments, the body of the ocular implant exhibits superelastic properties. The body may be made of nickel and titanium in appropriate proportions, such as, e.g., wherein the weight percent of nickel is between about 29.5 and about 50.5 weight percent and the weight percent of titanium is between about 29.5 and about 50.5 weight percent, based upon the total weight percent of the alloy.

In some embodiments of the ocular implant, the body extends through an arcuate range between about 60 degrees and about 180 degrees. A therapeutic agent may be deposited on the implant body in some embodiments. The therapeutic agent may be an anti-glaucoma drug, such as a prostaglandin analog (e.g., latanprost).

Another aspect of the invention provides a method of treating a human eye, including the steps of: inserting an implant into Schlemm's canal of a human eye, the implant having a first flexibility when bent along a first plane and a second flexibility different from the first flexibility when bent along a second plane that intersects the first plane and is not coincident with the first plane; and supporting tissue forming Schlemm's canal with the implant.

In some embodiments, the implant has an elongate slot, the method further including the step of orienting the elongate slot radially outward within Schlemm's canal. In some embodiments, the orienting step is performed at least in part by permitting the implant to self-orient with the canal. Some embodiments also add the step of providing fluid communication between an anterior chamber and the canal through the implant.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 7A is a lateral cross-sectional view of the ocular implant of FIG. 6 taken along section line A-A of FIG. 6.

FIG. 7B is a lateral cross-sectional view of the ocular implant of FIG. 6 taken along section line B-B of FIG. 6.

DETAILED DESCRIPTION OF THE INVENTION

Figure 1:
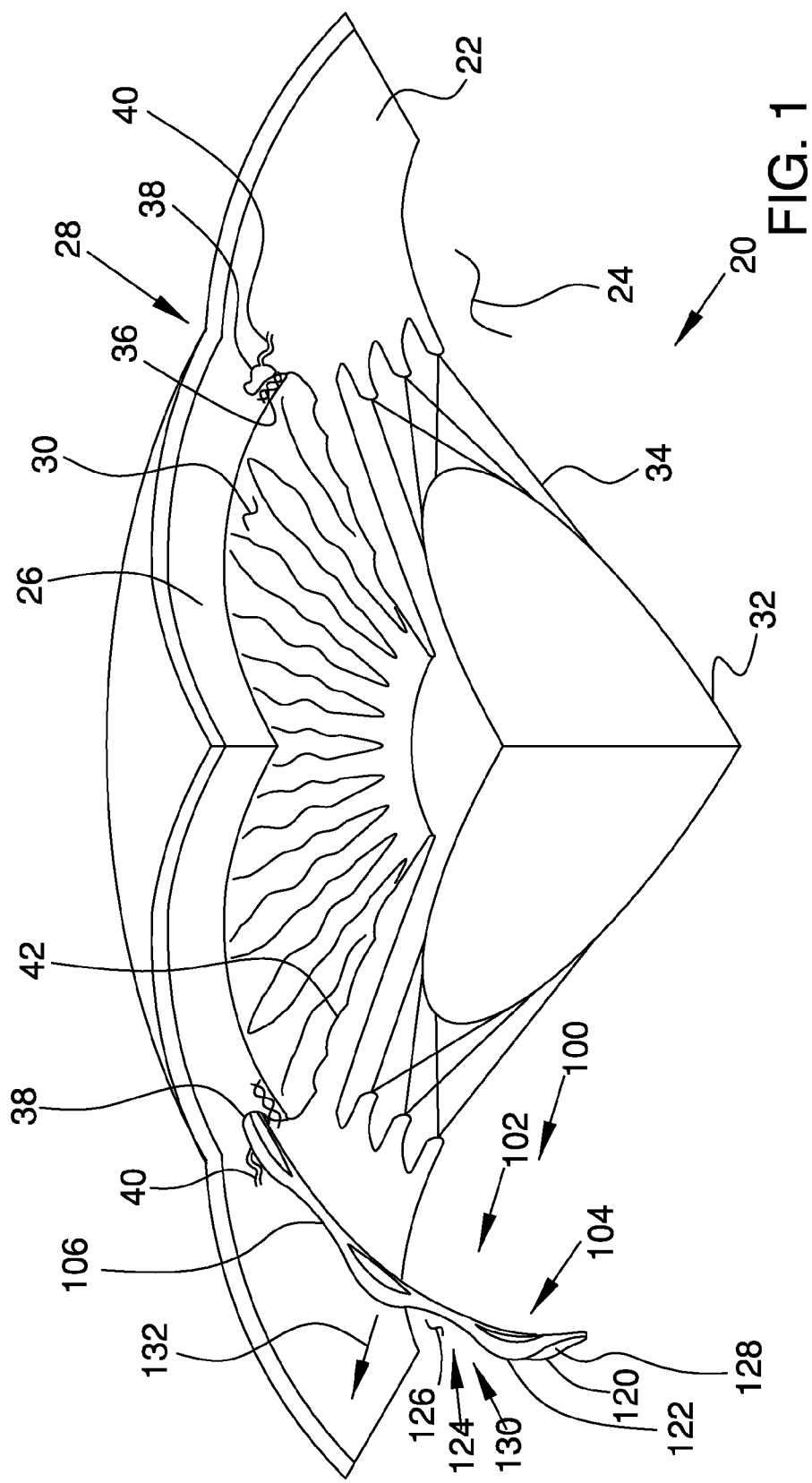
FIG. 1 is a stylized perspective view depicting a portion of a human eye and a portion of an ocular implant disposed in Schlemm's canal.

FIG. 1 is a stylized perspective view depicting a portion of a human eye 20. Eye 20 can be conceptualized as a fluid filled ball having two chambers. Sclera 22 of eye 20 surrounds a posterior chamber 24 filled with a viscous fluid known as vitreous humor. Cornea 26 of eye 20 encloses an anterior chamber 30 that is filled with a fluid know as aqueous humor. The cornea 26 meets the sclera 22 at a limbus 28 of eye 20. A lens 32 of eye 20 is located between anterior chamber 30 and posterior chamber 24. Lens 32 is held in place by a number of ciliary zonules 34.

Whenever a person views an object, he or she is viewing that object through the cornea, the aqueous humor, and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the eye as new aqueous humor is secreted by the epithelial cells of the ciliary body. This excess aqueous humor enters the blood stream and is carried away by venous blood leaving the eye.

In a healthy eye, aqueous humor flows out of the anterior chamber 30 through the trabecular meshwork 36 and into Schlemm's canal 38, located at the outer edge of the iris 42. Aqueous humor exits Schlemm's canal 38 by flowing through a number of outlets 40. After leaving Schlemm's canal 38, aqueous humor is absorbed into the venous blood stream.

In FIG. 1, an ocular implant 100 is disposed in Schlemm's canal 38 of eye 20. Ocular implant 100 has a body 102 including a plurality of tissue supporting frames 104 and a plurality of spines 106. Body 102 also includes a first edge 120 and a second edge 122 that define a first opening 124. First opening 124 is formed as a slot and fluidly communicates with an elongate channel 126 defined by an inner surface 128 of body 102. With reference to FIG. 1, it will be appreciated that first opening 124 is disposed on an outer side 130 of body 102. Accordingly, channel 126 opens in a radially outward direction 132 via first opening 124.

Ocular implant 100 may be inserted into Schlemm's canal of a human eye to facilitate the flow of aqueous humor out of the anterior chamber. This flow may include axial flow along Schlemm's canal, flow from the anterior chamber into Schlemm's canal, and flow leaving Schlemm's canal via outlets communicating with Schlemm's canal. When in place within the eye, ocular implant 100 will support trabecular mesh tissue and Schlemm's canal tissue and will provide for improved communication between the anterior chamber and Schlemm's canal (via the trabecular meshwork) and between pockets or compartments along Schlemm's canal. As shown in FIG. 1, the implant is preferably oriented so that the first opening 124 is disposed radially outwardly within Schlemm's canal.

Figure 2:
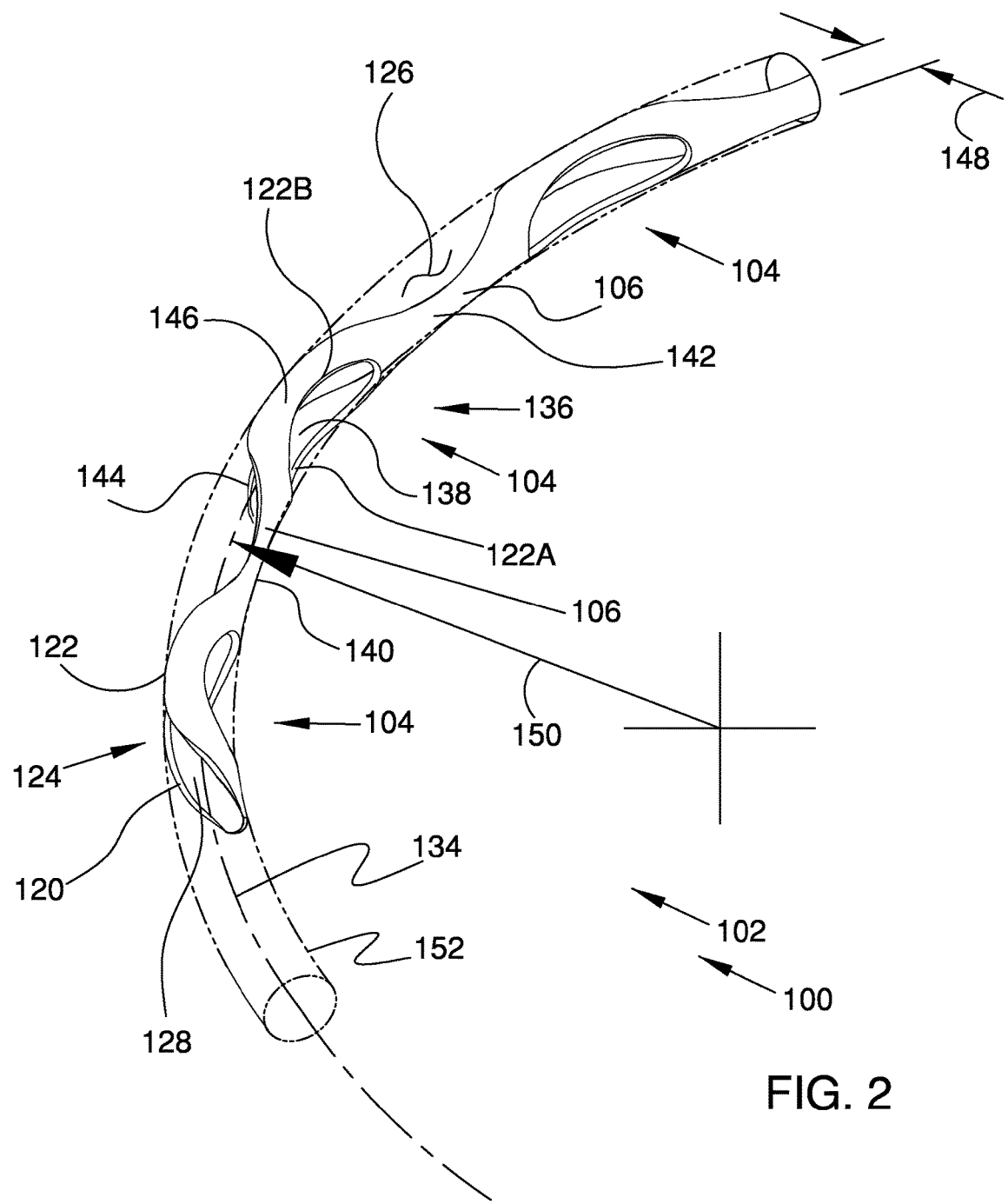
FIG. 2 is an enlarged perspective view showing a portion of the implant of FIG. 1.

FIG. 2 is an enlarged perspective view showing a portion of ocular implant 100 shown in the previous figure. Ocular implant 100 has a body 102 that extends along a generally curved longitudinal axis 134. Body 102 has a plurality of tissue supporting frames 104 and a plurality of spines 106. As shown in FIG. 2, these spines 106 and frames 104 are arranged in a repeating AB pattern in which each A is a tissue supporting frame and each B is a spine. In the embodiment of FIG. 2, one spine extends between each adjacent pair of frames 104

The frames 104 of body 102 include a first frame 136 of ocular implant 100 that is disposed between a first spine 140 and a second spine 142. In the embodiment of FIG. 2, first frame 136 is formed as a first strut 144 that extends between first spine 140 and second spine 142. First frame 136 also includes a second strut 146 extending between first spine 140 and second spine 142. In the exemplary embodiment of FIG. 2, each strut undulates in a circumferential direction as it extends longitudinally between first spine 140 and second spine 142.

In the embodiment of FIG. 2, body 102 has a longitudinal radius 150 and a lateral radius 148. Body 102 of ocular implant 100 includes a first edge 120 and a second edge 122 that define a first opening 124. First opening 124 fluidly communicates with an elongate channel 126 defined by an inner surface 128 of body 102. A second opening 138 is defined by a second edge 122A of a first strut 144 and a second edge 122B of a second strut 146. First opening 124, second opening 138 and additional openings defined by ocular implant 100 allow aqueous humor to flow laterally across and/or laterally through ocular implant 100. The outer surfaces of body 102 define a volume 152.

Figure 3:
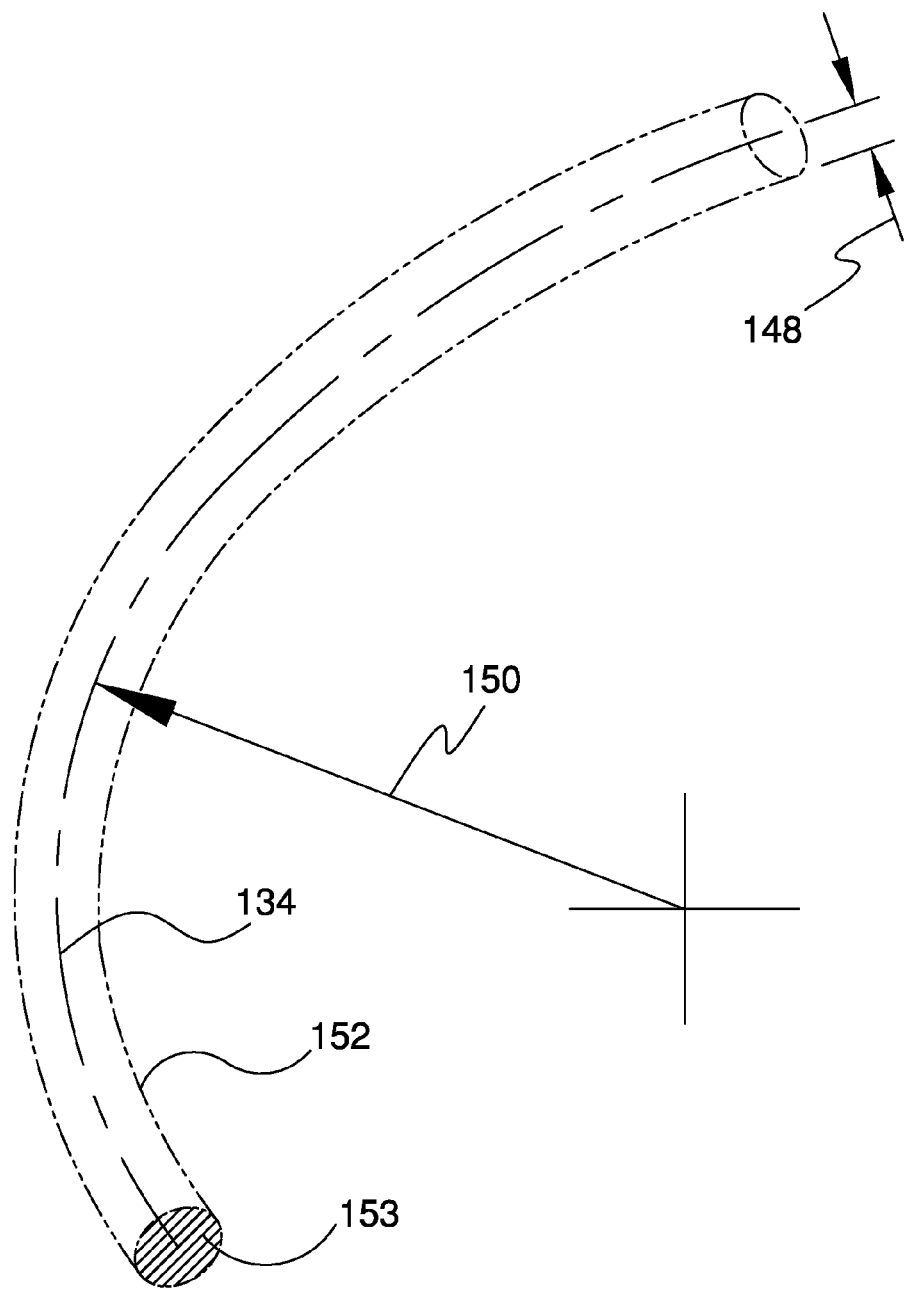
FIG. 3 is a perspective view showing a volume defined by the body of the ocular implant of FIGS. 1 and 2.

FIG. 3 is an additional perspective view showing volume 152 defined by the body of the ocular implant shown in the previous figure. With reference to FIG. 3, it will be appreciated that volume 152 extends along a generally curved longitudinal axis 134. Volume 152 has a longitudinal radius 150, a lateral radius 148, and a generally circular lateral cross section 153.

Figure 4:
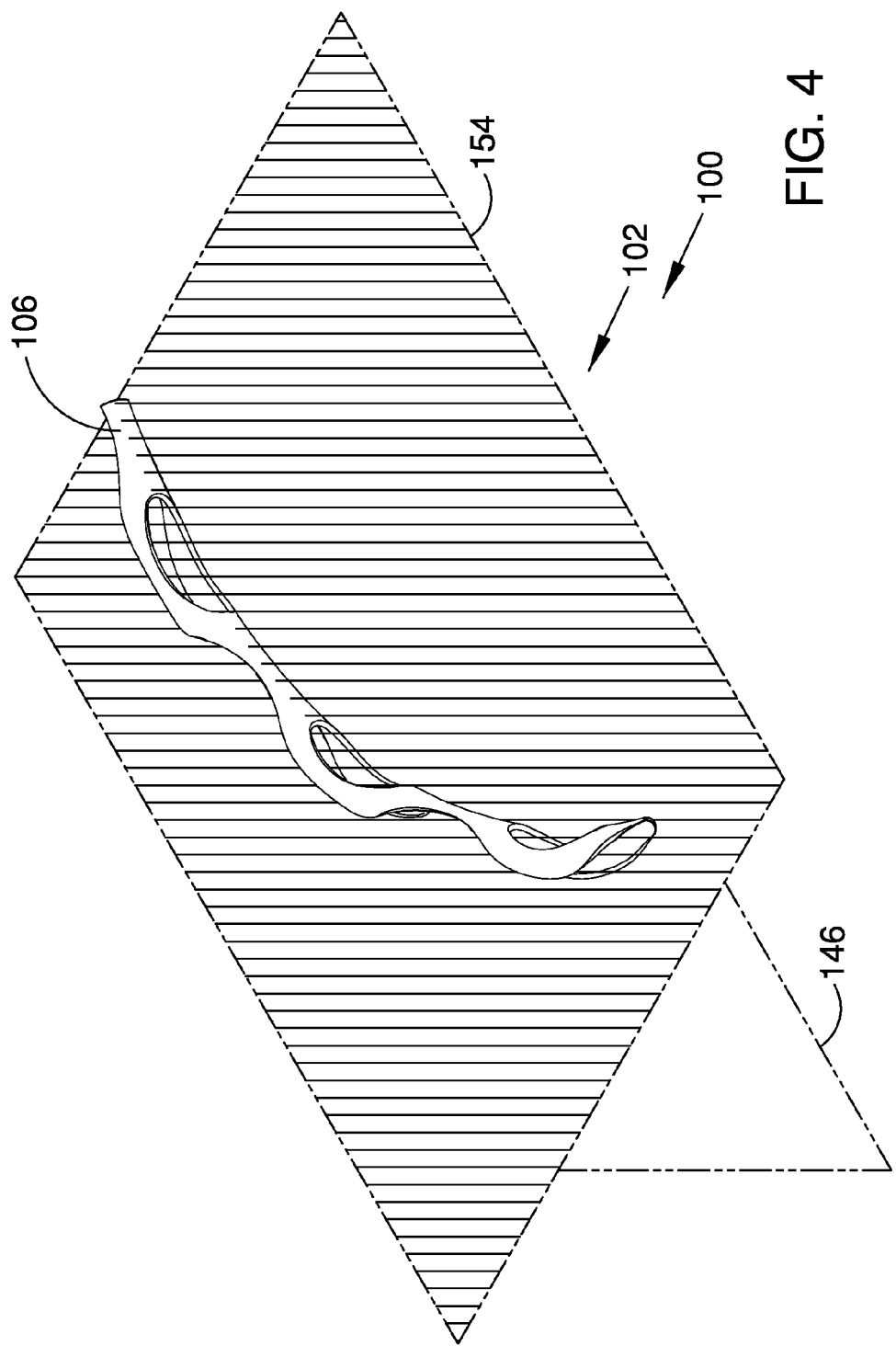
FIG. 4 is a perspective view showing a first plane intersecting the body of an ocular implant.

FIG. 4 is a perspective view showing a first plane 154 and a second plane 155 that both intersect ocular implant 100. In FIG. 4, first plane 154 is delineated with hatch marks. With reference to FIG. 4, it will be appreciated that spines 106 of body 102 are generally aligned with one another and that first plane 154 intersects all spines 106 shown in FIG. 4. In the embodiment of FIG. 4, body 102 of ocular implant 100 is generally symmetric about first plane 154.

In the embodiment of FIG. 4, the flexibility of body 102 is at a maximum when body 102 is bending along first plane 154, and body 102 has less flexibility when bending along a plane other than first plane 154 (e.g., a plane that intersects first plane 154). For example, in the embodiment shown in FIG. 4, body 102 has a second flexibility when bending along second plane 155 that is less than the first flexibility that body 102 has when bending along first plane 154.

Stated another way, in the embodiment of FIG. 4, the bending modulus of body 102 is at a minimum when body 102 is bent along first plane 154. Body 102 has a first bending modulus when bent along first plane 154 and a greater bending modulus when bent along a plane other than first plane 154 (e.g., a plane that intersects first plane 154). For example, in the embodiment shown in FIG. 4, body 102 has a second bending modulus when bent along second plane 155 that is greater than the first bending modulus that body 102 has when bent along first plane 154.

Figure 5:
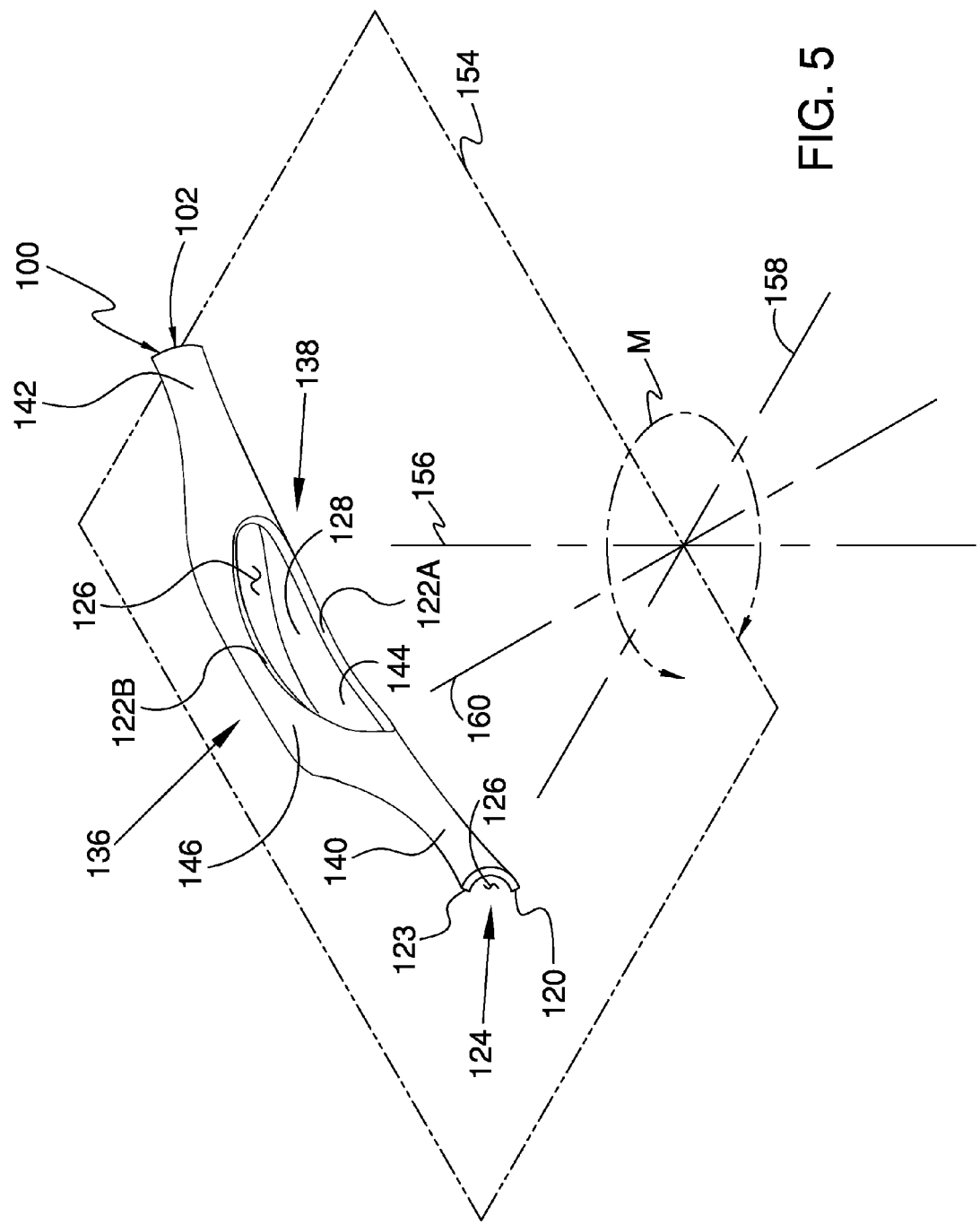
FIG. 5 is a perspective view showing a bending moment being applied to an ocular implant.

FIG. 5 is an enlarged perspective view showing a portion of ocular implant 100 shown in the previous figure. In the exemplary embodiment of FIG. 5, a bending moment M is being applied to body 102 of ocular implant 100. Bending moment M acts about a first axis 156 that is generally orthogonal to first plane 154. A second axis 158 and a third axis 160 are also shown in FIG. 5. Second axis 158 is generally perpendicular to first axis 156. Third axis 160 is skewed relative to first axis 156.

An inner surface 128 of body 102 defines a channel 126. Body 102 of ocular implant 100 includes a first edge 120 and a second edge 123 that define a first opening 124. Channel 126 of ocular implant 100 fluidly communicates with first opening 124. A second opening 138 is defined by a second edge 122A of a first strut 144 and a second edge 122B of a second strut 146. First opening 124, second opening 138 and additional openings defined by ocular implant 100 allow aqueous humor to flow laterally across and/or laterally through ocular implant 100.

As shown in FIG. 5, ocular implant 100 has a first spine 140 and a second spine 142. First strut 144 and a second strut 146 form a first frame 136 of ocular implant 100 that extends between first spine 140 and second spine 142. In the exemplary embodiment of FIG. 5, each strut undulates in a circumferential direction as it extends longitudinally between first spine 140 and second spine 142.

In the embodiment of FIG. 5, the flexibility of body 102 is at a maximum when body 102 is bent by a moment acting about first axis 156, and body 102 has less flexibility when bent by a moment acting about an axis other than first axis 156 (e.g., second axis 158 and third axis 160). Stated another way, the bending modulus of body 102 is at a minimum when body 102 is bent by a moment acting about first axis 156, and body 102 has a greater bending modulus when bent by a moment acting about an axis other than first axis 156 (e.g., second axis 158 and third axis 160).

Figure 6:
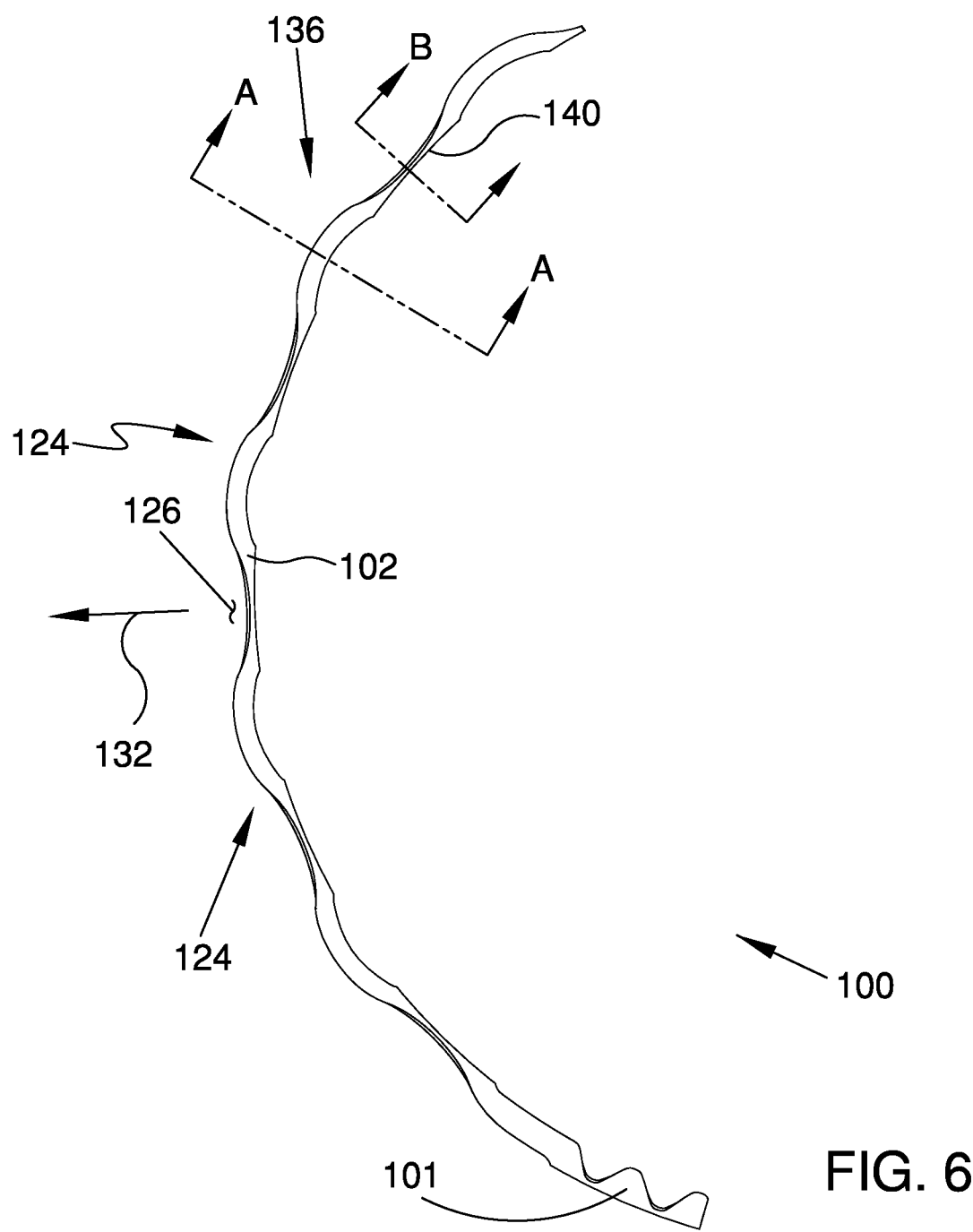
FIG. 6 is a plan view of the implant shown in FIG. 5 but in the absence of any bending moment.

FIG. 6 is a plan view showing ocular implant 100 shown in the previous figure. In the embodiment of FIG. 6, no external forces are acting on body 102 of ocular implant 100, and body 102 is free to assume the generally curved resting shape depicted in FIG. 6. Body 102 defines a first opening 124 that is disposed on an outer side 130 of body 102. A channel 126 is defined by the inner surface of body 102 and opens in a radially outward direction 132 via first opening 124.

Section lines A-A and B-B are visible in FIG. 6. Section line A-A intersects a first frame 136 of ocular implant 100. Section line B-B intersects a first spine 140 of ocular implant 100.

FIG. 7A is a lateral cross-sectional view of ocular implant 100 taken along section line A-A shown in the previous figure. Section line A-A intersects a first strut 144 and a second strut 146 of first frame 136 at the point where the circumferential undulation of these struts is at its maximum. Body 102 of ocular implant 100 has a longitudinal radius 150 and a lateral radius 148. An inner surface 128 of body 102 defines a channel 126. A first opening 124 fluidly communicates with channel 126.

In FIG. 7A, first opening 124 in body 102 can be seen extending between first edge 120A of first strut 144 and a first edge 120B of second strut 146. With reference to FIG. 7A, it will be appreciated that second strut 146 has a shape that is a mirror image of the shape of first strut 144.

FIG. 7B is a lateral cross-sectional view of ocular implant 100 taken along section line B-B shown in the previous figure. Section line B-B intersects first spine 140 of ocular implant 100. Body 102 has a longitudinal radius 150 and a lateral radius 148. In the embodiment of FIG. 7B, the center 159 of lateral radius 148 and the center 163 of longitudinal radius 150 are disposed on opposite sides of first spine 140. The center 159 of lateral radius 148 is disposed on a first side of first spine 140. The center 163 of longitudinal radius 150 is disposed on a second side of second spine 142.

Figure 8:
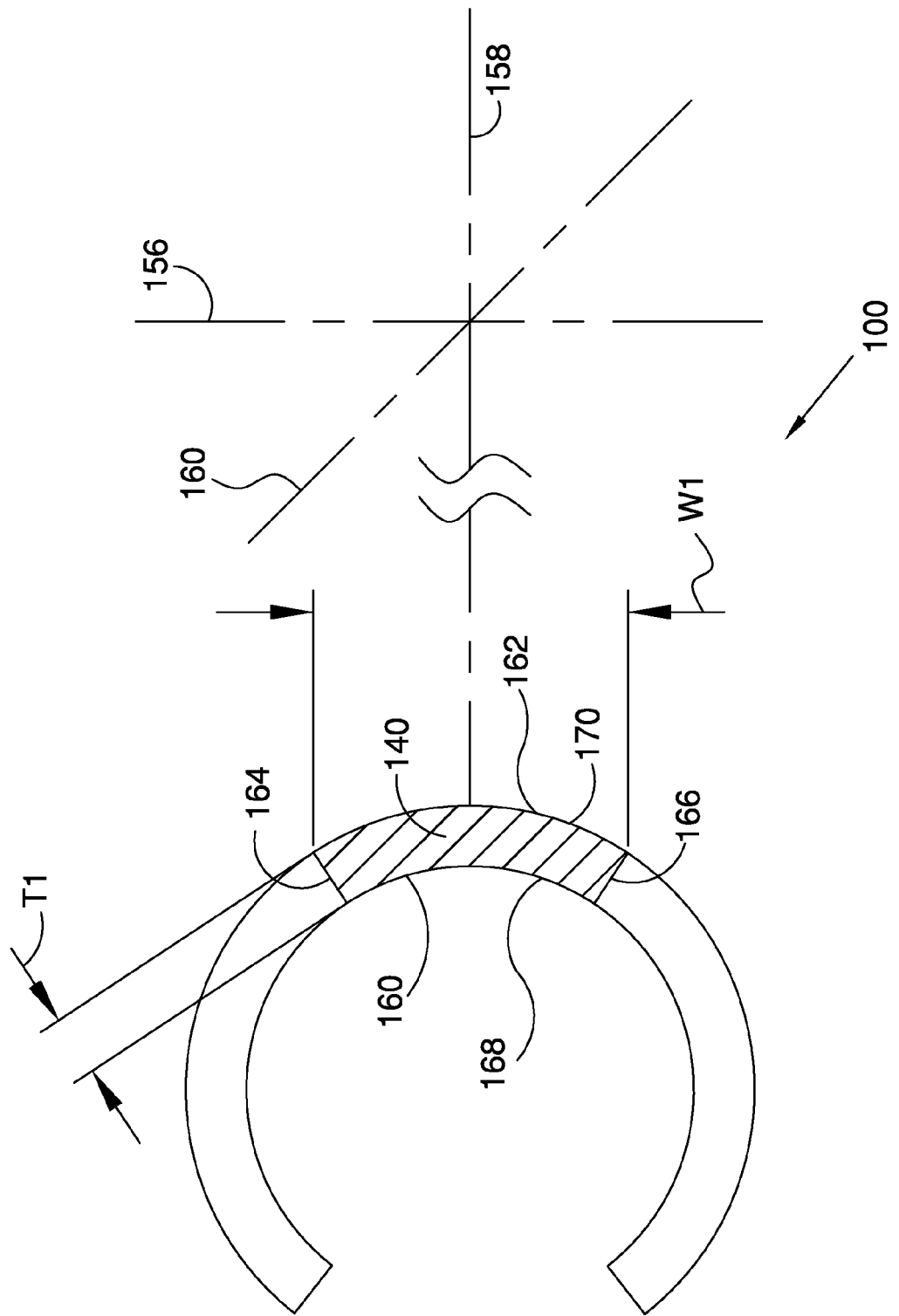
FIG. 8 is an enlarged cross-sectional view of the ocular implant of FIG. 6 taken along section line B-B of FIG. 6.

FIG. 8 is an enlarged cross-sectional view of ocular implant 100 taken along section line B-B of FIG. 6. First spine 140 includes a first major side 160, a second major side 162, a first minor side 164, and second minor side 166. With reference to FIG. 8, it will be appreciated that first major side 160 comprises a concave surface 168. Second major side 162 is opposite first major side 160. In the embodiment of FIG. 8, second major side 162 comprises a convex surface 170.

The geometry of the spine provides the ocular implant with flexibility characteristics that may aid in advancing the ocular implant into Schlemm's canal. In the embodiment of FIG. 8, first spine 140 has a thickness T1 extending between first major side 160 and second major side 162. Also in the embodiment of FIG. 8, first spine 140 has a width W1 extending between first minor side 164 and second minor side 166.

In some useful embodiments, the spine of an ocular implant in accordance with this detailed description has an aspect ratio of width W1 to thickness T1 greater than about 2. In some particularly useful embodiments, the spine of an ocular implant in accordance with this detailed description has an aspect ratio of width W1 to thickness T1 greater than about 4. In one useful embodiment, the ocular implant has a spine with an aspect ratio of width W1 to thickness T1 of about 5.2.

A first axis 156, a second axis 158 and a third axis 160 are shown in FIG. 8. Second axis 158 is generally perpendicular to first axis 156. Third axis 160 is skewed relative to first axis 156.

In the embodiment of FIG. 8, the flexibility of first spine 140 is at a maximum when first spine 140 is bent by a moment acting about first axis 156. First spine 140 has a first flexibility when bent by a moment acting about first axis 156 and less flexibility when bent by a moment acting about an axis other than first axis 156 (e.g., second axis 158 and third axis 160). For example, first spine 140 has a second flexibility when bent by a moment acting about second axis 158 shown in FIG. 8. This second flexibility is less than the first flexibility that first spine 140 has when bent by a moment acting about first axis 156.

In the embodiment of FIG. 8, the bending modulus of first spine 140 is at a minimum when first spine 140 is bent by a moment acting about first axis 156. First spine 140 has a first bending modulus when bent by a moment acting about first axis 156 and a greater bending modulus when bent by a moment acting about an axis other than first axis 156 (e.g., second axis 158 and third axis 160). For example, first spine 140 has a second bending modulus when bent by a moment acting about second axis 158 shown in FIG. 8. This second bending modulus is greater than the first bending modulus that first spine 140 has when bent by a moment acting about first axis 156.

Figure 9:
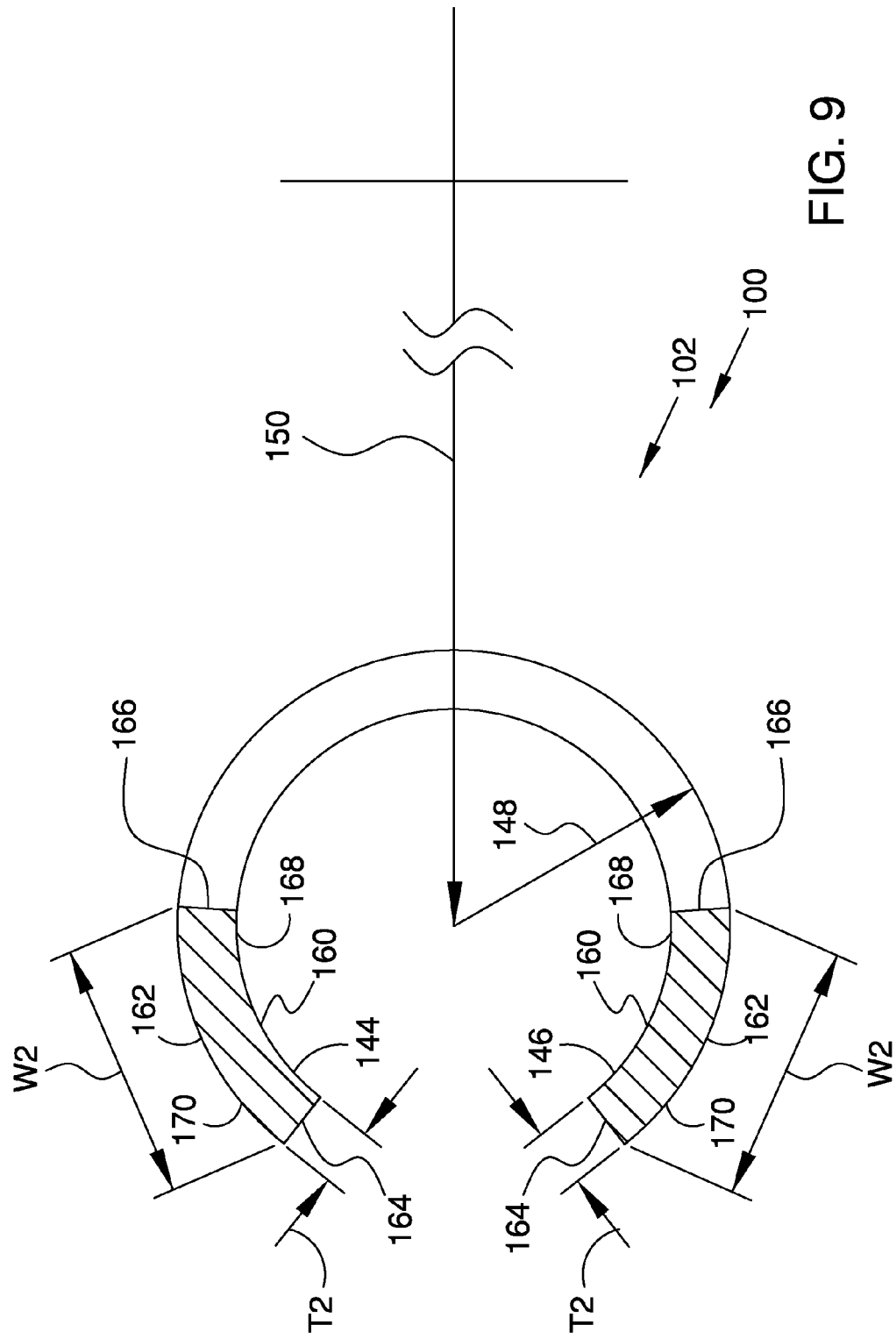
FIG. 9 is an enlarged cross-sectional view of the ocular implant of FIG. 6 taken along section line A-A of FIG. 6.

FIG. 9 is an enlarged cross-sectional view of ocular implant 100 taken along section line A-A of FIG. 6. Section line A-A intersects first strut 144 and second strut 146 at the point where the circumferential undulation of these struts is at its maximum.

Each strut shown in FIG. 9 includes a first major side 160, a second major side 162, a first minor side 164, and second minor side 166. With reference to FIG. 9, it will be appreciated that each first major side 160 comprises a concave surface 168 and each second major side 162 comprises a convex surface 170.

In the embodiment of FIG. 9, each strut has a thickness T2 extending between first major side 160 and second major side 162. Also in the embodiment of FIG. 9, each strut has a width W2 extending between first minor side 164 and second minor side 166. In some useful embodiments, an ocular implant in accordance with this detailed description includes spines having a width W1 that is greater than the width W2 of the struts of the ocular implant.

In some useful embodiments, the struts of an ocular implant in accordance with this detailed description have an aspect ratio of width W2 to thickness T2 greater than about 2. In some particularly useful embodiments, the struts of an ocular implant in accordance with this detailed description have an aspect ratio of width W2 to thickness T2 greater than about 4. One exemplary ocular implant has struts with an aspect ratio of width W2 to thickness T2 of about 4.4.

Body 102 of ocular implant 100 has a longitudinal radius 150 and a lateral radius 148. In some useful embodiments, an ocular implant in accordance with this detailed description is sufficiently flexible to assume a shape matching the longitudinal curvature of Schlemm's canal when the ocular implant advanced into the eye. Also in some useful embodiments, a length of the ocular implant is selected so that the implant will extend across a pre-selected angular span when the implant is positioned in Schlemm's canal. Examples of pre-selected angular spans that may be suitable in some applications include 60°, 90°, 150° and 180°. The diameter of an ocular implant in accordance with this detailed description may be selected so that the ocular implant is dimensioned to lie within and support Schlemm's canal. In some useful embodiments, the diameter of the ocular implant ranges between about 0.005 inches and about 0.04 inches. In some particularly useful embodiments, the diameter of the ocular implant ranges between about 0.005 inches and about 0.02 inches.

Figure 10:
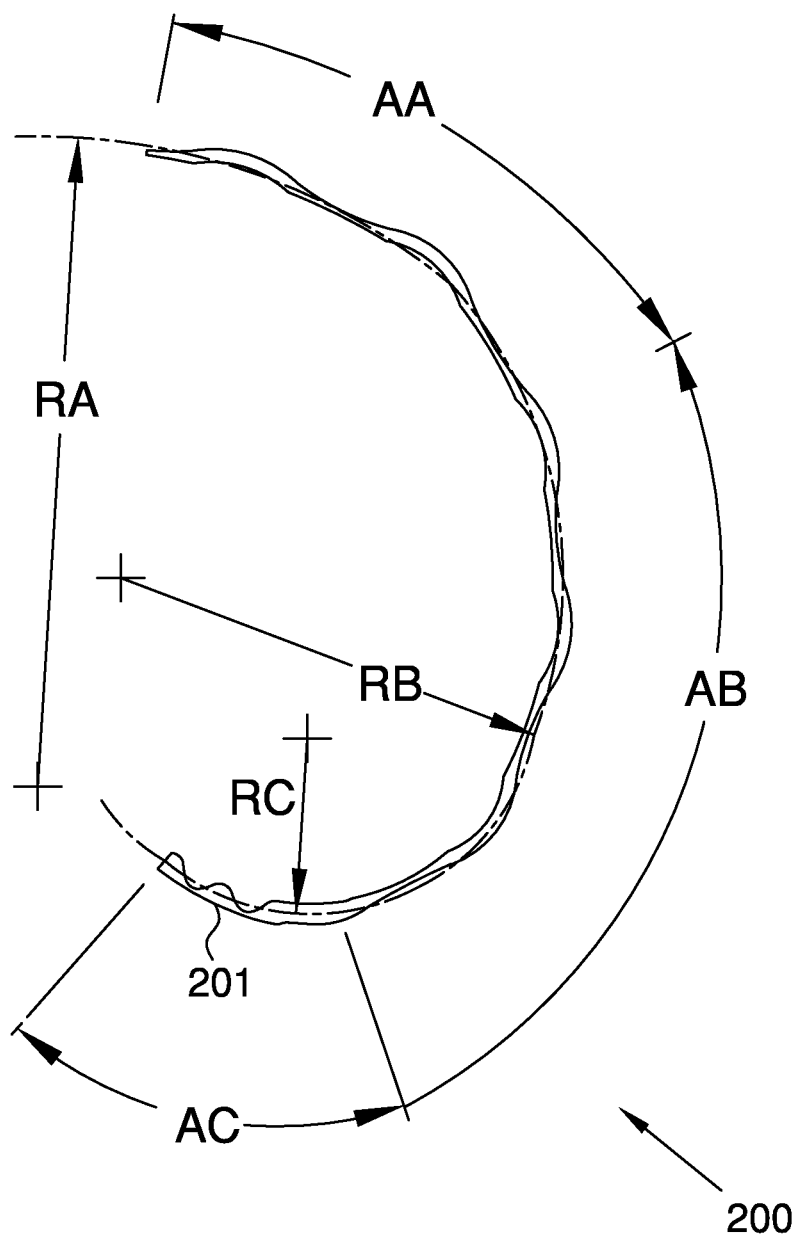
FIG. 10 is a plan view showing an ocular implant according to another embodiment of the invention having a longitudinal radius of curvature that varies along its length.
Figure 11:
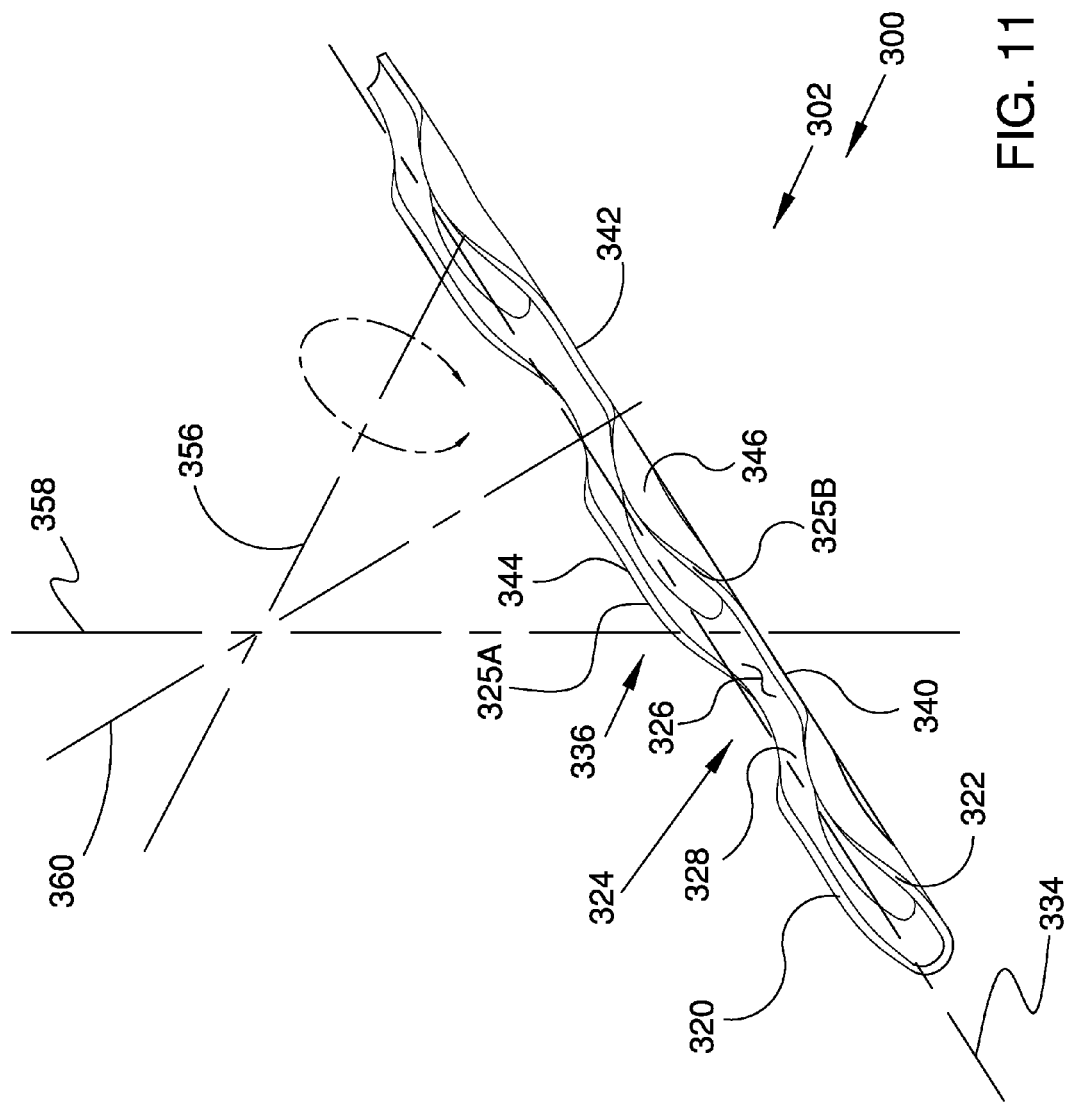
FIG. 11 is a perspective view showing an ocular implant according to yet another embodiment of the invention that has substantially no radius of curvature.

It is to be appreciated that an ocular implant in accordance with the present detailed description may be straight or curved. If the ocular implant is curved, it may have a substantially uniform longitudinal radius throughout its length, or the longitudinal radius of the ocular implant may vary along its length. FIG. 6 shows one example of an ocular implant having a substantially uniform radius of curvature. FIG. 10 shows one example of an ocular implant having a longitudinal radius of curvature that varies along the length of the ocular implant. An example of a substantially straight ocular implant is shown in FIG. 11.

FIG. 10 is a plan view showing an ocular implant 200 having a radius of curvature that varies along its length. In the embodiment of FIG. 10, ocular implant 200 has an at rest shape that is generally curved. This at rest shape can be established, for example, using a heat-setting process. The ocular implant shape shown in FIG. 10 includes a distal radius RA, a proximal radius RC, and an intermediate radius RB. In the embodiment of FIG. 10, distal radius RA is larger than both intermediate radius RB and proximal radius RC. Also in the embodiment of FIG. 10, intermediate radius RB is larger than proximal radius RC and smaller than distal radius RA. In one useful embodiment, distal radius RA is about 0.320 inches, intermediate radius RB is about 0.225 inches and proximal radius RC is about 0.205 inches.

In the embodiment of FIG. 10, a distal portion of the ocular implant follows an arc extending across an angle AA. A proximal portion of the ocular implant follows an arc extending across an angle AC. An intermediate portion of the ocular implant is disposed between the proximal portion and the distal portion. The intermediate portion extends across an angle AB. In one useful embodiment, angle AA is about 55 degrees, angle AB is about 79 degrees and angle AC is about 60 degrees.

Ocular implant 200 may be used in conjunction with a method of treating the eye of a human patient for a disease and/or disorder (e.g., glaucoma). Some such methods may include the step of inserting a core member into a lumen defined by ocular implant 200. The core member may comprise, for example, a wire or tube. The distal end of the ocular implant may be inserted into Schlemm's canal. The ocular implant and the core member may then be advanced into Schlemm's canal until the ocular implant has reached a desired position. In some embodiments, an inlet portion of the implant may be disposed in the anterior chamber of eye while the remainder of the implant extends through the trabecular mesh into Schlemm's canal. The core member may then be withdrawn from the ocular implant, leaving the implant in place to support tissue forming Schlemm's canal. Further details of ocular implant delivery systems may be found in U.S. application Ser. No. 11/943,289, filed Nov. 20, 2007, now U.S. Pat. No. 8,512,404, the disclosure of which is incorporated herein by reference.

The flexibility and bending modulus features of the ocular implant of this invention help ensure proper orientation of the implant within Schlemm's canal. FIG. 1 shows the desired orientation of opening 124 when the implant 100 is disposed in Schlemm's canal. As shown, opening 124 faces radially outward. The implant 100 is therefore designed so that it is maximally flexible when bent along a plane defined by the longitudinal axis of implant 100 as shown in FIG. 1, and less flexible when bent in other planes, thereby enabling the curved shape of Schlemm's canal to help place the implant in this orientation automatically if the implant is initially placed in Schlemm's canal in a different orientation.

FIG. 11 is a perspective view showing an ocular implant 300 in accordance with an additional embodiment in accordance with the present detailed description. With reference to FIG. 11, it will be appreciated that ocular implant 300 has a resting (i.e., unstressed) shape that is generally straight. Ocular implant 300 extends along a longitudinal axis 334 that is generally straight. In some useful embodiments, ocular implant 300 is sufficiently flexible to assume a curved shape when advanced into Schlemm's canal of an eye.

Ocular implant 300 comprises a body 302. With reference to FIG. 11, it will be appreciated that body 302 comprises a plurality of tissue supporting frames 304 and a plurality of spines 306. As shown in FIG. 11, these spines 306 and frames 304 are arranged in an alternating pattern in which one spine extends between each adjacent pair of frames 304. The frames 304 of body 302 include a first frame 336 of ocular implant 300 is disposed between a first spine 340 and a second spine 342. In the embodiment of FIG. 11, first frame 336 comprises a first strut 344 that extends between first spine 340 and second spine 342. A second strut 346 of first frame also extends between first spine 340 and second spine 342. Each strut undulates in a circumferential direction as it extends longitudinally between first spine 340 and second spine 342.

An inner surface 328 of body 302 defines a channel 326. Body 302 of ocular implant 300 includes a first edge 320 and a second edge 322 that define a first opening 324. Channel 326 of ocular implant 300 fluidly communicates with first opening 324. First strut 344 of first frame 336 comprises a first edge 325A. Second strut 346 has a first edge 325B. In FIG. 11, first opening 324 in body 302 can be seen extending between first edge 325A of first strut 344 and a first edge 325B of second strut 346.

A first axis 356, a second axis 358 and a third axis 360 are shown in FIG. 11. Second axis 358 is generally perpendicular to first axis 356. Third axis 360 is generally skewed relative to first axis 356. The flexibility of body 302 is at a maximum when body 302 is bent by a moment acting about first axis 356, and body 302 has less flexibility when bent by a moment acting about an axis other than first axis 356 (e.g., second axis 358 and third axis 360). Stated another way, in the embodiment of FIG. 11, the bending modulus of body 302 is at a minimum when body 302 is bent by a moment acting about first axis 356, and body 302 has a greater bending modulus when bent by a moment acting about an axis other than first axis 356 (e.g., second axis 358 and third axis 360).

Many of the figures illustrating embodiments of the invention show only portions of the ocular implant. It should be understood that many embodiments of the invention include an inlet portion (such as inlet 101 in FIG. 6 and inlet 201 in FIG. 10) that can be placed within the anterior chamber to provide communication of aqueous humor from the anterior chamber through the trabecular mesh into Schlemm's canal via the ocular implant. Further details of the inlet feature may be found in parent case U.S. application Ser. No. 11/860,318.

Various fabrication techniques may be used to fabricate the ocular implant. For example, the ocular implant can be fabricated by providing a generally flat sheet of material, cutting the sheet of material, and forming the material into a desired shape. By way of a second example, the ocular implant may be fabricated by providing a tube and laser cutting openings in the tube to form the ocular implant.

The ocular implant of this invention can be fabricated from various biocompatible materials possessing the necessary structural and mechanical attributes. Both metallic and non-metallic materials may be suitable. Examples of metallic materials include stainless steel, tantalum, gold, titanium, and nickel-titanium alloys known in the art as Nitinol. Nitinol is commercially available from Memry Technologies (Brookfield, Conn.), TiNi Alloy Company (San Leandro, Calif.), and Shape Memory Applications (Sunnyvale, Calif.).

The ocular implant may include one or more therapeutic agents. One or more therapeutic agents may, for example, be incorporated into a polymeric coating that is deposited onto the outer surfaces of the struts and spines of the ocular implant. The therapeutic agent may comprise, for example, an anti-glaucoma drug. Examples of anti-glaucoma drugs include prostaglandin analogs. Examples of prostaglandin analogs include latanprost.

While exemplary embodiments of the present invention have been shown and described, modifications may be made, and it is therefore intended in the appended claims to cover all such changes and modifications which fall within the true spirit and scope of the invention.

What is claimed is:

1. An ocular implant adapted to reside at least partially in a portion of Schlemm's canal of a human eye, the implant comprising:
    a body configured to extend within the Schlemm's canal, the body having a curved volume, a large radius side and a short radius side, wherein a radius of the short radius side is less than a radius of the large radius side, the body having a circumferential extent within the curved volume that varies along the length of the body between sections having a lesser circumferential extent and sections having a greater circumferential extent, one of the sections of lesser circumferential extent being disposed at a distal end of the body, the body defining a channel extending longitudinally through the body to and through the distal end of the body, the channel having an open side disposed on the large radius side at one of the sections of lesser circumferential extent and an adjacent section of greater circumferential extent and a plurality of openings along the length of the body on the short radius side, the openings being in fluid communication with the channel;
    an inlet portion configured to be disposed in an anterior chamber of the eye when the body is in the Schlemm's canal, the inlet portion disposed on a proximal end of the body in fluid communication with the channel, the inlet portion defining one or more openings adapted to be in fluid communication with the anterior chamber of the eye when the body is disposed in the Schlemm's canal; and
    a distally facing sloped surface at the distal end of the body formed by edges of one of the sections of lesser circumferential extent at the distal end of the body and edges of a section of greater circumferential extent proximal to the one section of lesser circumferential extent at the distal end of the body.

2. The ocular implant of claim 1 wherein each section of greater circumferential extent comprises a respective pair of struts, the sections of greater circumferential extent being separated from each other by the sections of lesser circumferential extent comprising spine sections, the struts and spine sections defining the channel.

3. The ocular implant of claim 2 wherein a respective opening of the plurality of openings is disposed between its respective pair of struts.

4. The ocular implant of claim 1 wherein the plurality of openings are disposed opposite the open side of the channel.

5. The ocular implant of claim 1 wherein the plurality of openings are disposed 140°-150° from the open side of the channel.

6. The ocular implant of claim 1 wherein the body is adapted to extend longitudinally from a proximal end to the distal end at least about 60° around a circle formed by the Schlemm's canal.

7. The ocular implant of claim 1 wherein the ocular implant is configured to provide a material coverage of the Schlemm's canal of less than 50% over 90% of the ocular implant's length.

8. The ocular implant of claim 1 wherein the ocular implant has a resting shape extending longitudinally in a curve from a proximal end to the distal end.

9. The ocular implant of claim 8 wherein the resting shape forms an arc of a circle, the inlet portion lying along the arc.

10. The ocular implant of claim 1 wherein the inlet portion defines an open channel along at least a portion of its length, the open channel configured to be in fluid communication with the anterior chamber of the eye.

\* \* \* \* \*